United States Patent [19]

Sleigh et al.

[11] Patent Number: 4,891,366

[45] Date of Patent: Jan. 2, 1990

[54] NOVEL 2β,16β-DIAMINO-ANDROSTANES

[75] Inventors: Thomas Sleigh, Wishaw; David S. Savage, Newton Mearns; Robert Taylor, Airdrie, all of Scotland

[73] Assignee: Akzo N.V., Arnhem, Netherlands

[21] Appl. No.: 184,547

[22] Filed: Apr. 20, 1988

[30] Foreign Application Priority Data

Apr. 23, 1987 [GB] United Kingdom ............... 8709565

[51] Int. Cl.$^4$ .................. A61K 31/58; A61K 31/56; C07J 1/00; C07J 43/00
[52] U.S. Cl. .................. 514/176; 514/182; 540/95; 540/96; 260/317.5
[58] Field of Search ............. 260/397.5; 514/182, 514/176; 540/95, 96

[56] References Cited

PUBLICATIONS

Tuba, CA 93:72074v (1980).
Cronnelly et al., CA 99:453u (1983).
Carlyle et al, CA 93:155850w (1980).
Buckett et al., CA 79:132827r (1973).
Organon, CA 66:38148e (1967).
CA 106(19): 149492x and Br. J. Pharmacol. 90(3), 511-21, 1987, Gibb et al.
CA 106(13): 96065f and Anaesthesist, 35(11), 661-4, 1986, Gilly et al.
CA 106(11): 78049z and Semin. Anesth. 5(4), 304-11, 1986, Savarese et al.
CA 106(7): 43927g and Anesthesiology, 65(6), 572-8, 1986, A. F. Kopman.
CA 106(7): 43828a and Br. J. Anaesth, 58(11), 1285-9, 1986, Caldwell et al.
CA 106(7): 43405k and Anesth. Analg. (N.Y.), 65(12), 1319-23, 1986m, Meistelman et al.
CA 106(3): 12287u and Anesth. Anal. (N.Y.), 65(3), 245-51, 1986, Bencini et al.
CA 105(23): 202628h and Biomed. Environ. Mass Spectrom 13(7), 327-32, 1986, Castagnoli et al.
CA 104(17): 141740u and Acta. Med. Okayama 39(6), 471-80, 1985, Y. Ohta.
CA 103(23): 189629w and Br. J. Anaesth, 57(8), 782-95, 1985, Bencini et al.
CA 102(3): 2059x and J. Labelled Compd. Radiopharm, 21(5)455-69, 1984, Lehmann et al.
CA 99(15): 115998t and Br. J. Anaesth, 55(8), 703-14, 1983, Marshall et al.
CA 99(1): 455w and Anesthesiology, 58(5), 414-17, 1983, Day et al.
CA 98(8): 6488w and Proc. Int. Symp. Instrum. High Perform Thin Layer Chromatogr. 2nd 186-94, 1982, Ed. R. E. Kaiser.
CA 95(17): 144033x and Anaesthesist, 30(7), 329-33, 1981, Booij et al.
CA 93(5): 36853q and Br. J. Anaesth, 52(3), 313-17, 1980, Salt et al.
CA 92(19): 157540y and J. Pharm. Pharmacol., 31(12), 831-6, 1979, Durant et al.
CA 79(23): 132827r and J. Med. Chem. 16(10) 1116-24, 1973, Buckett et al.

*Primary Examiner*—Douglas W. Robinson
*Assistant Examiner*—Joseph A. Lipovsky
*Attorney, Agent, or Firm*—William M. Blackstone

[57] ABSTRACT

2β,16β-diamino-3α,17α-oxygenated androstanes having one quaternized group, process for the preparation of these compounds and pharmaceutical compositions comprising such compounds as the active ingredient. The aforementioned compounds are favourable neuromuscular blocking agents.

9 Claims, No Drawings

NOVEL 2β,16β-DIAMINO-ANDROSTANES

The present invention relates to novel 2β,16β-diamino-androstane derivatives, to processes for their preparation and to pharmaceutical compositions comprising such derivatives.

2β,16β-diamino-androstane derivatives are known from British Pat. No. 1,138,605. These known compounds are highly active neuromuscular blocking agents. Although some of the compounds disclosed have been employed clinically for many years there remains room for improvement.

One of the requirements for a good neuromuscular blocking agent is a high selectivity for the skeletal neuromuscular junction as distinct from autonomically controlled muscles in particular those in the heart. In addition a fast onset of action allows a shorter time to incubation which is a further safety factor in anaesthetic practice.

Surprisingly, a novel class of 17α-substituted, steroid compounds has been found with improved characteristics. In particular these compounds exhibit a faster onset and shorter duration of action than known non-depolarizing neuromuscular blocking agents in the corresponding epimeric 17β-series. Further these compounds are highly potent neuromuscular blocking agents.

Accordingly, the present invention is concerned with 2β,16β-diamino-3α,17α-oxygenated androstanes having one quaternized amino group and acid addition salts thereof and in particular with compounds having the quaternized group in the 16β-substituent and even more in particular with compounds having the formula

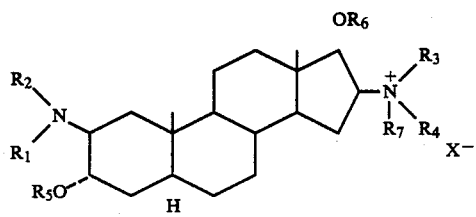

formula 1 wherein
$R_1$ and $R_2$ are hydrogen, an alkyl or aralkyl group having 1–10 carbon atoms, or when taken together form with the nitrogen atom a heterocyclic amino radical;
$R_3$ and $R_4$ are hydrogen, an alkyl or aralkyl group having 1–10 carbon atoms, or when taken together form with the nitrogen atom a heterocyclic amino radical;
$R_5$ is hydrogen or an acyl group having 1–12 carbon atoms;
$R_6$ is hydrogen or an acyl group having 1–12 carbon atoms;
$R_7$ is a hydrocarbyl group with 1–8 carbon atoms; and
$X^-$ is an anion, and acid addition salts thereof.

Some 2β,16β-diamino-17α-androstanes have been described in the Journal of Medicinal Chemistry 16, 1973, 1116–1124. However, these compounds are non-quaternary or bis-quaternary. No pharmacological data have been disclosed related to the non-quaternary compounds and the data disclosed with respect to the bis-quaternary compounds show a long duration of action and are silent with respect to onset and selectivity.

$R_1$ and $R_2$ may be an alkyl or aralkyl group having 1–10 carbon atoms, like methyl, ethyl, propyl, hexyl, phenyl, cumenyl, tolyl and xylyl preferably $R_1$ and $R_2$ when taken together with the nitrogen atom form a heterocyclic amino radical, like those derived from pyrrole, pyridine, indole, pyrimidine, piperazine, N-methylpiperazine, pyrrolidine, piperidine and morpholine. The most preferred radicals are the saturated radicals and especially those derived from pyrrolidine, piperidine and morpholine.

What has been described with respect to $R_1$ and $R_2$ applies to $R_3$ and $R_4$ as well. The heterocyclic amino radicals at positions 2β and 16β of the skeleton of the steroid may be the same or different.

$R_5$ and $R_6$ may be hydrogen or an acyl group having 1–12 carbon atoms like formyl, acetyl, propionyl, butyryl, valeryl, pivaloyl, propenoyl, 3-butenoyl and 4-pentenoyl. Preferably $R_5$ and $R_6$ are hydrogen or an acyl group having 1–4 carbon atoms. The groups $R_5$ and $R_6$ may be the same or different. As already said, the compounds according to the present invention contain one quaterized amino group. This quaternized amino group may be the amino group at position 2β or 16β or another amino group in the substituent at position 2β or 16β, like e.g. the amino group not attached to the 2β or 16β position if the substituent is piperazine or N-methylpiperazine. Preferably, the quaternized amino group is located in the substituent at position 16β. More preferably the quaternized amino group is the amino group attached to carbon atom 16 of the steroid skeleton. $R_7$ is a hydrocarbyl group having 1–8 carbon atoms, such as methyl, ethyl, ethynyl, propyl, allyl, propargyl, butyl, isobutyl, pentyl, cyclopropyl, cyclopropylmethyl and cyclohexyl. Preferably $R_7$ is an alkyl or alkenyl group with 1–4 carbon atoms. The anion in the quaternary ammonium derivatives may in principle be any pharmaceutically acceptable organic or inorganic anion, such as methylsulphonate, p-toluene sulphonate, $Cl^-$, $Br^-$ or $I^-$, and preferably the anion is $Br^-$.

The acid addition salts of the above compounds according to the present invention may be derived from any pharmaceutically acceptable organic or inorganic acid, such as hydrochloric acid, hydrobromic acid, hydro-iodic acid, nitric acid, sulphuric acid, phosphoric acid, acetic acid, propionic acid, butyric acid, caproic acid, malonic acid, succinic acid, glutaric acid, maleic acid, fumaric acid, tartaric acid, malic acid, pyruvic acid, lactic acid and citric acid.

Most preference is given to 1-[(2β, 3α, 5α,16β,17α)-3-acetyloxy-17-(1-oxo-propoxy)-2-(1-pipe-ridinyl)-androstan-16-yl]-1-methylpiperidinium bromide and its acid addition salt. The compounds according to the invention can be prepared by methods employing steps known or obvious to those skilled in the art.

The process for the preparation of the compounds according to claim 1 is characterized in that one amino group of a 2β, 16β-diamino-3α,17α-oxygenated androstane is quaternized and that subsequently, if desired, the compound obtained is reacted with water and/or is converted into its acid addition salt. In particular compounds according to claim 2 are prepared by reacting a compound having the formula

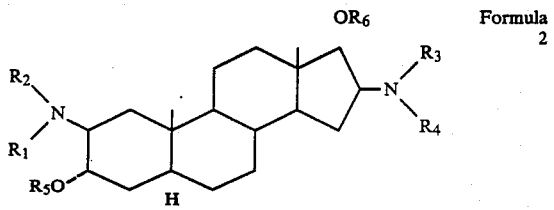

Formula 2 wherein $R_1$–$R_6$ have the same meaning as in claim 2, with a compound having the formula $R_7X$, wherein $R_7$ and X have the same meaning as in claim 2, so as to prepare the corresponding 16β-quaternary compound by methods obvious to those skilled in the art and that subsequently, if desired, the compound obtained is reacted with water and/or is converted into its acid addition salt.

The above starting compounds may be prepared by methods known per se or obvious to those skilled in the art. Starting from 5α-androst-2-en-17-one or 5α-androstan-3β-ol-17-one the preparation of these compounds has been disclosed in the Examples.

The monoquaternary compounds may be prepared by reacting 2β, 16β-diamino-3α, 17α-oxygenated androstane with a compound $R_7X$. By such reaction monoquaternary compounds having the monoquaternary group in the substituent at position 2β or at position 16β are formed. These compounds may be separated from the reaction mixture and from each other, e.g. by chromatography or by fractional crystallisation. If the substituent at position 2β and/or 16β comprises an additional amino group, like in case said substituent is a 4'-methyl-piperazino group, monoquaternary compounds are obtained with a quaternized nitrogen atom which is not directly attached to the carbon atom at position 2 or 16 of the steroid skeleton. Preferably the molar ratio of the steroid and $R_7X$ is between 1:1 and 1:50 and more preferably between 1:2 and 1:20. The reaction may be carried out at 10°–50° C. and especially at room temperature. The reaction time is 5–50 h generally. For choice the reaction is carried out in a suitable organic solvent such as methylene chloride. After the reaction the compounds according to the present invention are separated from the reaction mixture, e.g. by chromatography or by fractional crystallisation. Also use can be made of the fact that the compounds with a monoquaternary group in the substituent at position 16β are sparingly soluble in certa e.g. ether; the reaction can be performed in the presence of such solvent so that such compounds precipitate during the reaction or after the reaction the precipitation from the reaction mixture is achieved by the addition of such solvent. The compounds according to the present invention are obtained substantially free of the non- or bis-quaternized compounds.

The acid addition salts of the compounds according to the present invention may be prepared in the usual way by reaction with a pharmaceutically acceptable organic or inorganic acid.

The present invention is further concerned with pharmaceutical compositions comprising at least one compound according to the present invention as the pharmaceutically active ingredient. Preferably the pharmaceutical composition is aqueous. Such compositions are prepared by dissolving the compound(s) according to the present invention in water under aseptic conditions. In the case of the acid addition salt, such a composition may also be prepared by combining a pharmaceutically acceptable acid with an aqueous solution of the 2β, 16β-diamino-3α, 17α-oxygenated androstane having one quaternized amino group. The compositions may further be stabilized, if desired, by the addition of a pharmaceutically acceptable buffer system, which buffers in the range of pH 3–4,5, such as an acetic acid/sodium acetate buffer or a citric acid/sodium phosphate buffer.

The present compounds are intended particularly for use in clinical practice to produce skeletal muscular paralysis during surgical operations.

The compounds are usually administered by intravenous injection, in initial dosages between 5 and 50 mg (bolus injection), followed if necessary by smaller supplementary dosages.

The present invention is further illustrated by way of the following examples.

EXAMPLE 1

4-Methylbenzenesulphonic acid hydrazide (525 g) and 4-methylbenzenesulphonic acid (5.25 g) were added to a hot, stirred solution of (5α)-androst-2-en-17-one (700 g) in ethanol (5.6 l) and the solution was heated under reflux for 8 h. The stirred mixture was cooled and further ethanol (1 l) was added to give 4-methylbenzenesulphonic acid [(5α)-androst-2-en-17-ylidene]hydrazide as a crystalline solid.

EXAMPLE 2

Methyllithium in diethylether solution (3.3 l; 1.5M) Was added portionwise over 45 min. to a suspension of the compound prepared in Example 1 (900 g) in dry diethyl ether (13.5 l) under a nitrogen atmosphere. The reaction temperature was kept between 0° C. and 14° C. during the addition, then the suspension was stirred at room temperature for 20 h. The mixture was cooled to 5° C., water was added cautiously and the layers were separated. The ether layer was washed with water to neutrality, dried ($Na_2SO_4$) and evaporated to give a gum. The product was dissolved in toluene and the solution was chromatographed on a column (35 cm×4.5 cm) of silica gel (0.063–0.2 mm). Elution with toluene yielded a fraction which was evaporated to give a yellow gum (452 g). A solution of the product (452 g) in toluene was filtered through a second column (30 cm×4.5 cm) of alumina (Fluka, basic type 5016A) to remove colour. Evaporation of the eluate gave an oil, which was crystallised from ethanol to give (5α)-androsta-2,16-diene as prisms.

EXAMPLE 3

Anhydrous sodium acetate (45.04 g) was added to a stirred solution of (5α)-androsta-2,16-diene (450.4 g) in chloroform (1.35 l) and the stirred mixture was cooled to −8° C. Peracetic acid in acetic acid solution (901 ml; 38–40% w/w) was added dropwise at such a rate that the temperature Was kept below 12° C. The mixture was stirred at 0–5° C. for 5 h. then set aside in a refrigerator overniqht. Water was added and the layers were separated. The organic phase was washed with aqueous sodium sulphite, water, dried ($Na_2SO_4$) and evaporated to give a solid. Recrystallisation from diethyl ether gave (2α, 3α, 5α,16α,17α)-2,3,16,17-diepoxy-androstane.

EXAMPLE 4

A solution of the compound prepared in Example 3 (20 g) in piperidine (90 ml) and water (10 ml) was heated in an autoclave at 165° C. for 14 h. The solution was concentrated, then cooled, and water was added to precipitate the product as a colourless gum. The product was leached with hot water to remove most of the piperidine, then dissolved in dichloromethane. The solution was washed with water, dried (Na$_2$SO$_4$) and evaporated to give a gum. A solution of the gum in dichloromethane was filtered through a column (12.5 cm×4.5 cm) of alumina (Fluka basic type 5016A) to remove colour. Evaporation of the eluate gave a gum, which crystallised from dichloromethane-diethyl ether to give (2β, 3α, 5α,16β, 17α)-2,16-di-(1-piperidinyl)-androstane-3,17-diol. Similarly prepared were: (2β, 3α, 5α, 16β, 17α)-2,16-di-(4-morpholinyl)-androstane-3,17-diol and (2β, 3α, 5α, 16β, 17α)-2,16-di-(1-pyrrolidinyl)-androstane-3,17-diol.

EXAMPLE 5

Acetyl chloride (11 ml) was added to a solution of the dipiperidinyl compound prepared in Example 4 (10 g) in dichloromethane (100 ml) and the solution was set aside at room temperature for 20 h. The solution was evaporated to dryness and the product was dissolved in dichloromethane. The solution was washed with aqueous sodium carbonate solution (5% w/v) and water, then dried (Na$_2$SO$_4$) and evaporated to give a yellow gum. A solution of the product in dichloromethane was filtered through a column (12.5 cm×4 cm) of alumina (Fluka basic type 5016A) to remove colour. Evaporation of the eluate gave (2β, 3α, 5α, 16β, 17α)-2,16-di-(1-piperidinyl)-androstane-3,17-diol diacetate. Similarly prepared were:

(2β, 3α, 5α, 16β, 17α)-2,16-di-(1-piperidinyl)-androstane-3,17-diol dipropionate;
(2β, 3α,5α, 16β,17α)-2,16-di-(4-morpholinyl)-androstane-3,17-diol diacetate and
(2β, 3α, 5α, 16β, 17α)-2-(4-morpholinyl)-16-(1-piperidinyl)-androstane-3,17-diol diacetate.

EXAMPLE 6

A solution of the dipyrrolidinyl compound prepared in Example 4 (6.8 g) in pyridine (40 ml) and acetic anhydride (13.6 ml) was heated on a Water bath for 30 min. then set aside at room temperature overnight. Ice-water was added, followed by 5% aqueous sodium carbonate solution to precipitate an off-white solid, which was filtered off and washed with water. A solution of the product (7.4 g) in dichloromethane was dried (Na$_2$SO$_4$) and filtered through a column (12.5 cm×4 cm) of alumina (Fluka basic type 5016A) to remove impurities. Evaporation of the eluate gave (2β, 3α, 5α, 16β, 17α)-2,16-di-(1-pyrrolidinyl)-androstane-3,17-diol diacetate. Similarly prepared was: (2β, 3α, 5α, 16β, 17α)-16-(1-piperidinyl)-2-(1-pyrrolidinyl)-androstane-3,17-diol diacetate.

EXAMPLE 7

Acetyl chloride (68 ml) was added dropwise to a stirred solution of (2β, 3α, 5α, 16β, 17α)-2,16-di-(1-piperidinyl)-androstane-3,17-diol (360 g) in dichloromethane (2.5 l) at °C. and the solution was set aside at room temperature for 18 h. The solution was concentrated and the product was precipitated as the hydrochloride on the addition of acetone. The hydrochloride was recrystallised from dichloromethane-acetone, then dissolved in water. Aqueous sodium carbonate solution (5% w/v) was added and the mixture was extracted with dichloromethane. The organic layer was washed with water, dried (Na$_2$SO$_4$) and evaporated to give a gum (221.2 g). A solution of the product in dichloromethane was chromatographed on alumina (1 kg; Fluka basic type 5016A). Elution with dichloromethane yielded a fraction, which was evaporated to give (2β, 3α, 5α, 16β, 17α)-2,16-di-(1-piperidinyl)-androstane-3,17-diol 3-acetate.

Butanoyl chloride (95 ml) was added to a solution of this compound (191.25 g) in dichloromethane (1.91 l) and the solution was set aside at room temperature for 20 h. The solution was evaporated to give a gum, which was dissolved in dichloromethane. The solution was washed with aqueous sodium carbonate solution (5% w/v) and water, then dried (Na$_2$SO$_4$) and concentrated to 1 l. The solution was filtered through a column of alumina (35 cm×6.5 cm; Fluka basic type 5016A) to remove much of the colour. Elution with dichloromethane yielded a fraction, which was evaporated to give (2β, 3α, 5α, 16β, 17α)-2,16-di-(1-piperidinyl)- androstane-3,17-diol 3-acetate 17-butanoate. Similarly prepared were:

(2β, 3α, 5α, 16β, 17α)-2,16-di-(1-piperidinyl)-androstane-3,17-diol 3-acetate 17-propanoate and
(2β, 3α, 5α, 16β, 17α)-2,16-di-(1-piperidinyl)-androstane-3,17-diol 3-acetate 17-(2,2-dimethylpropanoate).

EXAMPLE 8

A solution of the dipiperidinyl-diacetate compound prepared in Example 5 (0.5 g) in methanol (4.5 ml) and water (0.5 ml) was boiled under reflux for 3 h., during which time (2β, 3α, 5α, 16β, 17α)-2,16-di-(1-piperidinyl)-androstane-3,17-diol 17-acetate (0.32 g) crystallised out.

EXAMPLE 9

4-Methylbenzenesulphonyl chloride (20 g) was added to a stirred solution of (3β, 5α)-androst-16-en-3-ol (20 g), which was prepared from (3β, 5α)-androstan-3-ol-17-one in a similar way as described in Examples 1 and 2, in pyridine (100 ml) at °C. The mixture was stirred at 0°-5° C. for 1 h., then set aside in a refrigerator for 3 d. Water was added to precipitate the product as off-white prisms. Recrystallisation from diethyl ether-methanol gave colourless prisms of (3β, 5α)-androst-16-en-3-ol 4-methylbenzenesulphonate, Which Was treated as described in Example 3.

The resulting (3β, 5α, 16α, 17α)-16,17-epoxy-androstan-3-ol 4-methylbenzenesulphonate (153 g) was added over 5 min., under a nitrogen atmosphere to 1,8-diazabicyclo[5.4.0]undec-7-ene (153 ml) which had been heated to 130° C. After 10 min., the reaction temperature rose rapidly to 150° C. and the reaction flask was removed from the oil bath. The solution was cooled, poured into water with stirring and the precipitated solid was filtered off and dried at 60° C. in vacuo. A solution of the product in dichloromethane was chromatographed on silica gel (475 g; 0.063–0.2 mm). Elution with dichloromethane gave a fraction, which was evaporated to give a gum (70 g). Crystallisation from dichloromethane-diethyl ether gave (5α,16α,17α)-16,17-epoxy-androst-2-ene (55.2 g). From this compound the following compounds were made in a manner similar to Example 4:

(5α, 16β, 17α)-16-(1-piperidinyl)-androst-2-en-17-ol,
(5α,16β,17α)-16-(1-pyrrolidinyl)-androst-2-en-17-ol, and
(5α, 16β, 17α)-16-diethylamino-androst-2-en-17-ol.

A solution of the (1-piperidinyl)-compound (2.75 g) and methyl 4-methylbenzenesulphonate (1.38 g) in methyl cyanide (20 ml) was heated under reflux for 5.5 h. The solution was evaporated to dryness to give a gum, which was crystallised from acetone to give 1-[(5α,16β, 17α)-17-hydroxy-androst-2-en-16-yl]-1-methylpiperidinium 4-methylbenzenesulphonate (2.80 g). Similarly prepared were:

1-[(5α, 16β,17α)-17-hydroxy-androst-2-en-16-yl]-1-methyl-pyrrolidinium-4-methylbenzenesulphonate, and (5α, 16β, 17α)-N,N-diethyl-17-hydroxy-N-methyl-androst-2-en-16-aminium 4-methylbenzenesulphonate.

A solution of 3-chlorobenzenecarboperoxoic acid (3.28 g) in dichloromethane (100 ml) was added to a solution of the piperidinium compound (6.4 g) in dichloromethane (64 ml) and the solution was set aside at room temperature for 17 h. The solution was concentrated to low volume then a large volume of diethyl ether was added to give a gum, which solidified on standing. The solid was filtered, washed with diethyl ether, and recrystallised from acetone to give 1-[(2β, 3α, 5α, 16β,17α)-2,3-epoxy-17-hydroxy-androstan-16-yl]-1-methylpiperidinium 4-methylbenzene-sulphonate. Similarly prepared were:

1-[(2β, 3α, 5α, 16β, 17α)-2,3-epoxy-17-hydroxy-androstan16-yl]- 1-methylpyrrolidinium 4-methy)-benzenesulphonate and (2α, 3α, 5α, 16β, 17α)-2,3-epoxy-N,N-diethyl-17-hydroxy-N-methyl-androstan-16-aminium 4-methylbenzenesulphonate.

A solution of the 2,3-epoxy-methylpiperidinium compound (30 g) in morpholine (135 ml) and water (15 ml) was heated under reflux for 6 d. The solution was cooled and water was added to precipitate a buff-coloured solid, which was filtered off and washed with water. A solution of the product (28 g) in dichloromethane-ethanol-ammonia (100:10:1 v/v) was chromatographed on silica gel (52 g). Elution with the same eluant mixture gave a fraction which was evaporated to dryness. The residue was crystallised from acetone to give .(2β, 3α, 5α, 16β, 17α)-2-(4-morpholinyl)-16-(1-piperidinyl)-androstane-3,17-diol (15 g).

Similarly prepared were (2β, 3α, 5α, 16β, 17α)-16-(1-piperidinyl)-2-(1-pyrrolidinyl)-androstane-3,17-diol, (2β, 3α, 5α, 16β, 17α)-2-(4-morpholinyl)-16-(1-pyrrolidinyl)-androstane-3,17-diol and (2β, 3α, 5α, 16β, 17α)-16-diethylamino-2-(1-piperidinyl)-androstane-3,17-diol.

EXAMPLE 10

Bromomethane (32.1 g) was added to a solution of the 17-butanoate compound prepared in Example 7 (21.4 g) in dichloromethane (428 ml) and the solution was set aside overnight at room temperature. The solution was evaporated to dryness to give a gum (28.5 g), which was dissolved in dichloromethane and chromatographed on alumina (650 g; Fluka basic type 5016A). Elution with dichloromethane gave a small amount of material (0.4 g), which was discarded, but elution with ethyl acetate-propan-2-ol (3:1 v/v) gave a froth (21.85 g), which was redissolved in dichloromethane. The solution was added dropwise, with stirring to dry diethyl ether to precipitate 1-[(2β, 3α, 5α, 16β, 17α)-3-(acetyloxy)-17-(1-oxobutoxy)-2-(1-piperidinyl)-androstan-16-yl]-1-methylpiperidinium bromide as a fine, crystalline solid (19.08 g), m.p. 194°–195° C., $[\alpha]_D^{20} = +34.5°$ (c 1.01 in $CHCl_3$), Similarly prepared were:

1-[(2β, 3α,5α, 16β, 17α)-3-(acetyloxy)-17-(1-oxobutoxy) -2-(1-piperidinyl)-androstan-16-yl]-1-(2-propenyl) piperidinium bromide, $[\alpha]_D^{20}1 = +30.4°$ (c 0.91 in $CHCl_3$), 1-[(2β, 3α, 5α, 16β, 17α)-3-(acetyloxy)-17-(1-oxobutoxy)-2-(1-piperidinyl)-androstan-16-yl]-1-ethylpiperidinium bromide, $[\alpha]_D^{20} = +31.8°$ (c 0.98 in $CHCl_3$), 1-[(2β, 3α, 5α, 16β, 17α)-3-(acetyloxy)-17-(1-oxopropoxy)-2-(1-piperidinyl)-androstan-16-yl]-1-methylpiperidinium bromide, m.p. 168°–173° C., $[\alpha]_D^{20} = +34.5°$ (c 1.02 in $CHCl_3$), 1-[(2β, 3α, 5α, 16β, 17α)-3-(acetyloxy)-17-(1-oxopropoxy)-2-(1-piperidinyl)-androstan-16-yl]-1-(2-propenyl) piperidinium bromide, m.p. 183°–187° C., $[\alpha]_D^{20} = 30.3°$ (c 1.08 in $CHCl_3$), 1-[(2β, 3α, 5α, 16β, 17α)-3-(acetyloxy)-17-(2,2-dimethyl-1-oxopropoxy)-2-(1-piperidinyl)-androstan-16-yl]-1-methylpiperidinium bromide, $[\alpha]_D^{20} = +30.9°$ (c 0.74 in $CHCl_3$), 1-[(2β, 3α, 5α, 16β, 17α)-3,17-bis(acetyloxy)-2-(1-piperidinyl)-androstan-16-yl]-1-methyl-piperidinium bromide, m.p. 200°–205° C., $[\alpha]_D^{20} = +33.7°$ (c 0.93 in $CHCl_3$), 1-[(2β, 3α, 5α, 16β, 17α)-3,17-bis(acetyloxy)-2-(1-piperidinyl)-androsaan-16-yl]-1-(2-propenyl) piperidinium bromide, $[\alpha]_D^{20} = +30.3°$ (c 1.44 in $CHCl_3$), 1-[(2β, 3α, 5α, 16β, 17α)-3,17-bis(1-oxopropoxy)-2-(1-piperidinyl)-androstan-16-yl]-1-methyl-piperidinium bromide, $[\alpha]_D^{20} = +32°$ (c 1.26 in $CHCl_3$), 1-[(2β, 3α, 5α, 16β, 17α)-3,17-bis(1-oxopropoxy)-2-(1piperidinyl]-androstan-16-yl]-1-(2-propenyl) piperidinium bromide, m.p. 194°–195° C., $[\alpha]_D^{20} = 28.8°$ (c 0.70 in $CHCl_3$), 1-[(2β, 3α, 5α, 16β, 17α)-17=(acetyloxy)-3-hydroxy-2-(1-piperidinyl-androstan-16-yl]-1-methyl-piperidinium bromide, $[\alpha]_D^{20} = +69.2°$ (c 1.21 in $CHCl_3$), 1-[(2β, 3α, 5α,16β, 17α)-17-(acetyloxy)-3-hydroxy-2-(1-piperidinyl)-androstan-16-yl]-1-(2-propenyl) piperidinium bromide, $[\alpha]_D^{20} = +64.9°$ (c 0.99 in $CHCl_3$), 4-[(2β, 3α, 5α, 16β, 17α)-3,17-bis(acetyloxy)-2-(4-morpholinyl)-androstan-16-yl]-4-methylmorpholinium bromide, m.p. 185°–187° C., $[\alpha]_D^{20} = +28.5°$ (c 0.96 in $CHCl_3$), 4-[(2β, 3α, 5α, 16β, 17α)-3,17-bis(acetyloxy)-2(4-morpholinyl)-androstan-16-yl]-4-(2-propenyl) morpholinium bromide, $[\alpha]_D^{20} = +28.4°$ (c 0.98 in $CHCl_3$), 1-[(2β, 3α, 5α, 16β, 17α)-3,17-bis(acetyloxy)-2-(1-pyrrolidinyl)-androstan-16-yl]-1-methylpyrrolidinium bromide, m.p. 172°–178° C. (decomp.), $[\alpha]_D^{20} = +34.9°$ (c 1.38 in $CHCl_3$), 1-[(2β, 3α, 5α, 6β, 17α)-3,17-bis(acetyloxy)-2-(1-pyrrolidinyl)-androstan-16-yl]-1-(2-propenyl) pyrrolidinium bromide, $[\alpha]_D^{20} = +34.9°$ (c 1.06 in $CHCl_3$), 1[(2β, 3α, 5α, 16β, 17α)-3-(acetyloxy)-17-hydroxy-2-(1- piperidinyl)-androstan-16-yl]-1-methyl-piperidinium bromide, m.p. 253°–258° C. (decomp.), $[\alpha]_D^{20} = +25.2°$ (c 0.94 in $CHCl_3$), 1-[(2β, 3α, 5α, 16β, 17α)-3,17-bis(acetyloxy)-2-(1-pyrrolidinyl)-androstan-16-yl]-1-methyl-piperidinium bromide, $[\alpha]_D^{20}=+32.6°$ (c 1.21 in CHCl$_3$), 1-[(2β, 3α, 5α, 16β, 17α)-3,17-bis(acetyloxy)-2-(1-pyrrolidinyl)-androstan-16-yl]-1-(2-propenyl) piperidinium bromide, $[\alpha]_D^{20}=+29.0°$ (c 0.87 in CHCl$_3$), 1-[(2β, 3α, 5α, 16β, 17α)-3,17-bis(acetyloxy)-2-(4-morpholinyl)-androstan-16-yl]-1-methyl-piperidinium bromide, m.p. 174–179° C., $[\alpha]_D^{20}=+30.5°$ (c 1.49 in CHCl$_3$), 1-[(2β, 3α, 5α, 16β, 17α)-3,17-bis(acetyloxy)-2-(4-morpholinyl)-androstan-16-yl]-1-(2-propenyl) piperidinium bromide, m.p. 157°–160° C., +27.0° (c 0.91 in CHCl$_3$), 1-[(2β, 3α, 5α, 16β, 17α)-3,17-dihydroxy-2-(1-piperidinyl)-androstan-16-yl]-1-methyl-piperidinium bromide, m.p. 243°–247° C. (decomp.), $[\alpha]_D^{20}=+67.0°$ (c 0.95 in CHCl$_3$),

EXAMPLE 11

A solution of 1-[(2β, 3α, 5α, 16β, 17α)-3-(acetyloxy)-17-(1-oxobutoxy)-2-(1-piperidinyl)-androstan-16-yl]-1-methylpiperidinium bromide (9 g) in water (360 ml) was set aside at room temperature for 15 d. The solution was filtered through dicalite and the filtrate was evaporated to low volume, then distilled azeotropically with toluene to remove water. A solution of the product (6.6 g) in dichloromethane was chromatographed on alumina (184 g; Fluka basic type 5016A). Elution with dichloromethane gave a fraction which was discarded. Elution With ethyl acetate-propan-2-ol (3:1 v/v and 2:1 v/v) yielded similar fractions, which were combined and evaporated to give a gum (3.6 g). A solution of the gum in dichloromethane was added dropwise with stirring to diethyl ether to precipitate-[(2β, 3α, 5α, 16β, 17α)-3-hydroxy-17-(1-oxobutyroxy)-2-(1-piperidinyl)-androstan-16-yl]-1-methylpiperidinium bromide, (3.17 g), $[\alpha]_D^{20}=+62.7°$ (c 1.12 in CHCl$_3$), Similarly prepared were:

1-[(2β, 3α, 5α, 16β, 17α)-17-(acetyloxy)-3-hydroxy-2-(1-pyrrolidinyl)-androetan-16-yl]-1-methylpyrrolidinium bromide, $[\alpha]_D^{20}=+35.6°$ (c 1.26 in CHCl$_3$), 1-[(2β, 3α, 5α, 16β, 17α)-17-(acetyloxy)-3-hydroxy-2-(1-pyrrolidinyl)-androstan-16-yl]-1-(2-propenyl) pyrrolidinium bromide, $[\alpha]_D^{20}=+36.5°$ (c 1.04 in CHCl$_3$), 1-[(2β, 3α, 5α, 16β, 17α)-17-(acetyloxy)-3-hydroxy-2-(1-pyrrolidinyl)-androstan-16-yl]-1-(2-propenyl) piperidinium bromide, $[\alpha]_D^{20}=+32.5°$ (c 0.75 in CHCl$_3$), 1-[(2β, 3α, 5α, 16β, 17α)-17-(acetyloxy)-3-hydroxy-2-(4-morpholinyl)-androstan-16-yl]-1-methyl-piperidinium bromide, m.p. 181°–185° C., $[\alpha]_D^{20}=+57.5°$ (c 1.03 in CHCl$_3$), and, 1-[(2β, 3α, 5α, 16β, 17α)-17-(acetyloxy)-3-hydroxy-2-(4-morpholinyl)-androstan-16-yl]-1-(2-propenyl) piperidinium bromide, m.p. 152°–157° C., $[\alpha]_D^{20}=53.2°$ (c 1.1 in CHCl$_3$).

EXAMPLE 12

Propanoyl chloride (1.5 ml) Was added to a solution of 1-[(2β, 3α, 5α, 16β, 17α)-17-(acetyloxy)-3-hydroxy-2-(1-piperidinyl)-androstan-16-yl]-1-methyl-piperidinium bromide, (1 g) in dichloromethane (20 ml) and the solution was set aside at room temperature for 22 h. The solution was evaporated to give a froth, which was dissolved in dichloromethane and re-precipitated by the addition of diethyl ether to give a sticky solid. A solution of the solid in dichloromethane was chromatographed on a column (14 cm×2.5 cm) of alumina (Fluka basic type 5016A). The dichloromethane eluate was discarded, but elution with ethyl acetate-propane-2ol (3:1 v/v) gave a gum (0.84 g) which was crystallised from acetone-diethyl ether to give 1-[(2β, 3α, 5α, 16β, 17α)-17-(acetyloxy)-3-(1-oxopropoxy)-2-(1-piperidinyl)-androstan-16-yl]-1-methylpeperidinium bromide, as colourless prisms (0.57 g), m.p. 177°–181° C., $[\alpha]_D^{20}=+33.6°$ (c 0.78 in CHCl$_3$). Similarly prepared Was:

1-[(2β, 3α, 5α, 16β, 17α)-17-(acetyloxy)-3-(1-oxopropoxy)-2-(1-piperidinyl)-androstan-16-yl]-1-(2-propenyl) piperidinium bromide, m.p. 197°–200° C., $[\alpha]_D^{20}+30.1°$ (c 0.84 in CHCl$_3$).

EXAMPLE 13

Hydrogen chloride gas Was passed through a solution of 1-[(2β, 3α, 5α, 16β, 17α)-3-(acetyloxy)-17-(1-oxobutoxy)-2-(1-piperidinyl)-androstan-16-yl]-1-methylpiperidinium bromide, (0.5 g) in dichloromethane (40 ml), then the solution was evaporated to give a froth. The product was dissolved in acetone and diethyl ether was added to precipitate an amorphous solid, Which Was filtered off and washed with ether. The solid was heated under reflux in acetone to give 1-[(2β, 3α, 5α, 16β, 17α)-3-(acetyloxy)-17-(1-oxobutoxy)-2-(1-piperidinyl)-androstan-16-yl]-1-methylpiperidinium bromide hydrochloride as prisms (0.45 g), m.p. 220°–228° C., $[\alpha]_D^{20}=+57.2°$ (c 1.32 in CHCl$_3$).

EXAMPLE 14

Similarly to the examples 9, 6 and 10 the following compounds were prepared (the name of the first compound has been given fully, for compounds 2–13 only the differences from the first compound have been indicated):

1. 1-[(2β, 3α, 5α, 16β, 17α)-3,17-bis(acetyloxy)-2-(1-piperidinyl)androstan-16-yl]hexahydro-1-methyl-1H-azepinium bromide, $[\alpha]_D^{20}=+37.0°$ (c=0.92 in CHCl$_3$);
2. the corresponding hexahydro-1-(2-propenyl)-1H-azepinium bromide, $[\alpha]_D^{20}=+36.5°$ (c=0.90 in CHCl$_3$);
3. the corresponding 3,17-bis-(1-oxopropoxy)hexahydro-1-(2-propenyl)-1H-azepinium bromide, $[\alpha]_D^{20}=+34.1°$ (c=0.92 in CHCl$_3$);
4. the corresponding 3,17-bis-(1-oxopropoxy) compound $[\alpha]_D^{20}=+36.0°$ (c=0.78 in CHCl$_3$);
5. the corresponding 3,17-bis-(1-oxobutoxy) compound $[\alpha]_D^{20}=32.7°$ (c=1.16 in CHCl$_3$);
6. the corresponding 2-(4-morpholinyl) compound, $[\alpha]_D^{20}=35.4°$ (c=1.08 in CHCl$_3$);
7. the corresponding 2-(4-morpholinyl)-hexadyro-1-(2-propenyl)-1H-azepinium bromide, $[\alpha]_D^{20}==+31.4°$ (c=1.08 in CHCl$_3$);
8. the corresponding 3,17-bis(1-oxopropoxy)-2-(4-morpholinyl) compound, $[\alpha]_D^{20}=+31.5°$ (c=0.87 in CHCl$_3$);
9. the corresponding 3,17-bis(1-oxopropoxy)-2-(4-morpholinyl)-hexahydro-1-(2-propenyl)-1H-azepinium bromide, $[\alpha]_D^{20}=+30.4°$ (c=0.63 in CHCl$_3$);

10. the corresponding 2-(hexahydro-1H-azepin-1-yl) compound, m.p.=159°–165° C. and $[\alpha]_D^{20}=42.6°$ (c=0.85 in CHCl$_3$);

11. the corresponding 2-(hexahydro-1H-azepin-1-yl)-hexahydro-1-(2-propenyl)-1H-azepinium bromide, m.p.=129°–134° C. and $[\alpha]_D^{20}=40.4°$ (c=0.81 in CHCl$_3$);

12. the corresponding 3,17-bis(1-oxopropoxy)-2-(hexahydro-1H-azepin-1-yl)-hexahydro-1-(2-propenyl)-1H-azepinium bromide, m.p.=137°–140° C. and $[\alpha]_D^{20}=+39.0$ (c=0.90 in CHCl$_3$); and 13. the corresponding 3,17-bis(1-oxopropoxy)-2-(hexahydro-1H-azepin-1-yl) compound, m.p.=157°–161° C. and $[\alpha]_D^{20}=+37.9°$ (c=0.89 in CHCl$_3$).

EXAMPLE 15

Similarly to the examples 9, 7 and 10 the following compounds were prepared (the name of the first compound has been given fully, for compounds 2–4 only the differences from the first compound have been indicated);

1. 1-[(2β, 3α, 5α, 16β, 17α)-3-(acetyloxy)-17-(1-oxobutoxy)-2-(1-piperidinyl)androstan-16-yl]-hexahydro-1-methyl-1H-azepinium bromide, $[\alpha]_D^{20}=+34.4°$ (c=1.17 in CHCl$_3$);

2. the corresponding 17-(1-oxopropoxy) compound, $[\alpha]_D^{20}=+35.2°$ (c=1.07 in CHCl$_3$);

3. the corresponding 17-(1-oxopropoxy)-2-(4-morpholinyl)hexahydro-1-(2-propenyl)-1H-azepinium bromide, m.p.=136°–139° C. and $[\alpha]_D^{20}=+31.2°$ (c=0.93 in CHCl$_3$); and 4. the corresponding; 17-(1-oxopropoxy)-2-(4-morpholinyl) compound, m.p.=170°–174° C. and $[\alpha]_D^{20}=+35.5°$ (c=0.92 in CHCl$_3$).

We claim:

1. 2β, 16β-diamino-3α, 17α-oxygenated androstanes having one quaternized amino group as a 16β-substituent, and acid addition salts thereof.

2. Compounds according to claim 1 having the formula

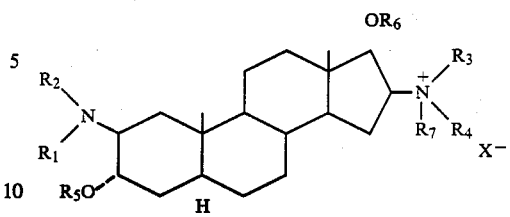

formula 1 wherein
R$_1$ and R$_2$ are hydrogen, an alkyl or aralkyl group having 1–10 carbon atoms, or when taken together form with the nitrogen atom a heterocyclic amino radical selected from the group consisting of pyrrole, pyridine, indole, pyrimidine, piperazine, N-methylpiperazine, pyrrolidine, piperidine, morpholine, and azepine;

R$_3$ and R$_4$ are hydrogen, an alkyl or aralkyl group having 1–10 carbon atoms, or when taken together form with the nitrogen atom a heterocyclic amino radical selected from the group consisting of pyrrole, pyridine, indole, pyrimidine, piperazine, N-methylpiperazine, pyrrolidine, piperidine, morpholine, and azepine;

R$_5$ is hydrogen or an acyl group having 1–12 carbon atoms;

R$_6$ is hydrogen or an acyl group having 1–12 carbon atoms; R$_7$ is a hydrocarbyl group with 1–8 carbon atoms; and X$^-$ is an anion, and acid addition salts thereof.

3. Compounds according to claim 2, wherein R$_1$ and R$_2$ form with the nitrogen atom a heterocyclic amino radical.

4. Compounds according to claim 2, wherein R$_3$ and R$_4$ form with the nitrogen atom a heterocyclic amino radical.

5. Compounds according to claim 2, wherein R$_5$ is hydrogen or an acyl group having 1–4 carbon atoms.

6. Compounds according to claim 2, wherein R$_6$ is hydrogen or an acyl group having 1–4 carbon atoms.

7. Compounds according to claim 2, wherein R$_7$ is an alkyl or alkenyl group with 1–4 carbon atoms.

8. Pharmaceutical composition comprising at least one compound according to claim 1 in a therapeutically effective amount for use as a neuromuscular blocking agent and a pharmaceutically acceptable carrier.

9. 1-[(2β,3α,5α,16β,17α)-3-acetyloxy-17-(1-oxopropoxy)-2-(1-piperidinyl)-androstan-16-yl]-1-methylpiperidinium bromide.

* * * * *